(12) United States Patent
Yi et al.

(10) Patent No.: US 9,299,925 B2
(45) Date of Patent: Mar. 29, 2016

(54) MULTI-PURPOSE SENSOR

(71) Applicants: Ge Yi, San Ramon, CA (US); Dujiang Wan, Fremont, CA (US)

(72) Inventors: Ge Yi, San Ramon, CA (US); Dujiang Wan, Fremont, CA (US)

( * ) Notice: Subject to any disclaimer, the term of this patent is extended or adjusted under 35 U.S.C. 154(b) by 145 days.

(21) Appl. No.: 14/161,699

(22) Filed: Jan. 23, 2014

(65) Prior Publication Data

US 2015/0204647 A1    Jul. 23, 2015

(51) Int. Cl.
| | |
|---|---|
| *G01B 7/14* | (2006.01) |
| *H01L 43/14* | (2006.01) |
| *G01D 5/00* | (2006.01) |
| *G01H 11/00* | (2006.01) |
| *A61B 5/11* | (2006.01) |
| *G01C 9/06* | (2006.01) |
| *G01P 15/03* | (2006.01) |
| *G01P 15/105* | (2006.01) |
| *G01P 15/11* | (2006.01) |
| *G01P 15/125* | (2006.01) |
| *G01P 15/18* | (2013.01) |
| *G08B 21/04* | (2006.01) |
| *A63B 24/00* | (2006.01) |
| *G01D 5/14* | (2006.01) |
| *G01D 5/20* | (2006.01) |
| *G01D 5/24* | (2006.01) |
| *G01V 1/00* | (2006.01) |

(52) U.S. Cl.
CPC .............. *H01L 43/14* (2013.01); *A61B 5/1117* (2013.01); *G01C 9/06* (2013.01); *G01D 5/00* (2013.01); *G01H 11/00* (2013.01); *G01P 15/036* (2013.01); *G01P 15/105* (2013.01); *G01P 15/11* (2013.01); *G01P 15/125* (2013.01); *G01P 15/18* (2013.01); *G08B 21/043* (2013.01); *G08B 21/0446* (2013.01); *A61B 2562/0223* (2013.01); *A63B 24/0062* (2013.01); *G01D 5/145* (2013.01); *G01D 5/2013* (2013.01); *G01D 5/24* (2013.01); *G01V 1/008* (2013.01)

(58) Field of Classification Search
None
See application file for complete search history.

(56) References Cited

U.S. PATENT DOCUMENTS 5,983,724 A * 11/1999 Yoshida ............... H01H 35/147
73/652
9,153,114 B2 * 10/2015 Yi ...................... G08B 21/0446

* cited by examiner

*Primary Examiner* — Minh N Tang

(57) ABSTRACT

A three-dimensional sensor system made from an assembly of three either semi- or fully independently oriented sensors, each of which has a working principle based on detecting the movement of a floating magnet supported by magnetic levitation. The sensor system can be used for fall detecting, tilting monitoring and vibration tracking. The volume fabrication method of making individual sensor for such as system is also given.

14 Claims, 15 Drawing Sheets

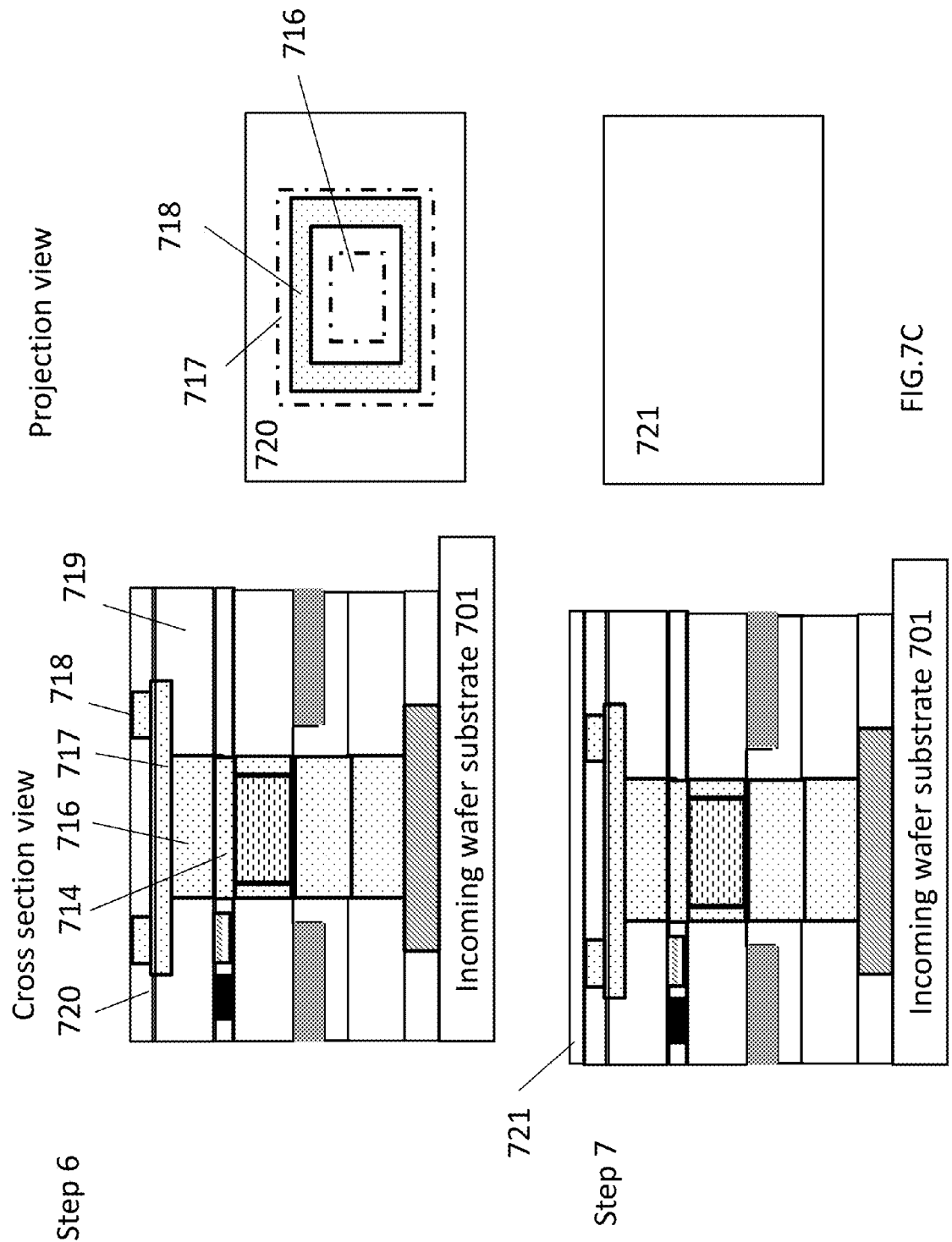

MULTI-PURPOSE SENSOR

FIELD OF INVENTION

The invention is related to a three axle sensor system, which can be used for fall detection, digital tilting angle measurement respect to local gravity, digital pulse/vibration measurement with great sensitivity. The individual sensor for the system can be made in volume production with proposed manufacture process disclosed in this patent.

BACKGROUND ART

Fall detection is very important and has widely applications in older care, patient care, child care, disable care as well as safety for outdoor sports event. To develop a reliable fall detection system has huge market potential and great society impact. Conventional fall detection system is designed to detect whether a real fall event happens by matching falling acceleration data with pre-set models or thresholds using enormous different kinds of algorithm. However, a random fall event depends on actual situation and prior falling movement of the host. It is too complicated to have a precise model to mimic the real event. Despite of great efforts, there is no a successful product existing on the market with great impact. The present invention resolves this dilemma by directly measuring/sensing the relative position/orientation between the host body and direction of gravity at the spot where a falling event happens.

Related to fall detection, measuring the tilt angle respect to local gravity is also very useful. Currently, tilting angle is also indirectly measured with reference to local gravity or ground mostly through measuring acceleration via an accelerometer or gyroscope.

Detecting vibration with great sensitivity also has many applications. Conventionally, vibration detection is carried out by accelerometer (e.g. piezoelectric sensor or capacitive sensor), velocity sensor (e.g. electromagnetic linear velocity transducer), proximity probes (e.g. capacitance or eddy current), or laser displacement sensor. In this invention, a brand new sensor is proposed, which can be used to fulfill the requirements for the above mentioned tilt sensor or vibration sensor applications. Several embodiments of the designs with respective sensitivity are proposed.

SUMMARY OF THE INVENTION

A new type of sensor system, which has multiple applications such as fall detection, dynamic tilting detection, and vibration detection, is disclosed. Several alternative designs of sensor with different sensitivity have been given. The manufacture processes, using semiconductor wafer process together with MEMS technology, have been described. This makes low-cost large scale manufacture of this type of sensor system feasible.

The individual sensor for each axle, having strong preferred uniaxial, can be used to detect the vibration of the membrane or the hard surface along its preferred axle. Based on this sensor, a new class of sonar technology can be developed.

With additional coil design for energy harvesting as an energy source, this invention becomes a self-powered multi-purpose sensor system.

Coupled with wireless technology, it can be used as a basic key component for large scale wireless sensor network.

Deploying in large scale in buoyant state in the targeted depth in middle of the sea this sensor system can be used to detect earthquake as well as tsunami in the deep sea as part of an alarming system.

DETAILED DESCRIPTION

The following description is provided in the context of particular designs, applications and the details, to enable any person skilled in the art to make and use the invention. However, for those skilled in the art, it is apparent that various modifications to the embodiments shown can be practiced with the generic principles defined here, and without departing the spirit and scope of this invention. Thus, the present invention is not intended to be limited to the embodiments shown in this disclosure, but is to be accorded the widest scope consistent with the principles, features and teachings disclosed here.

Figure 1B:
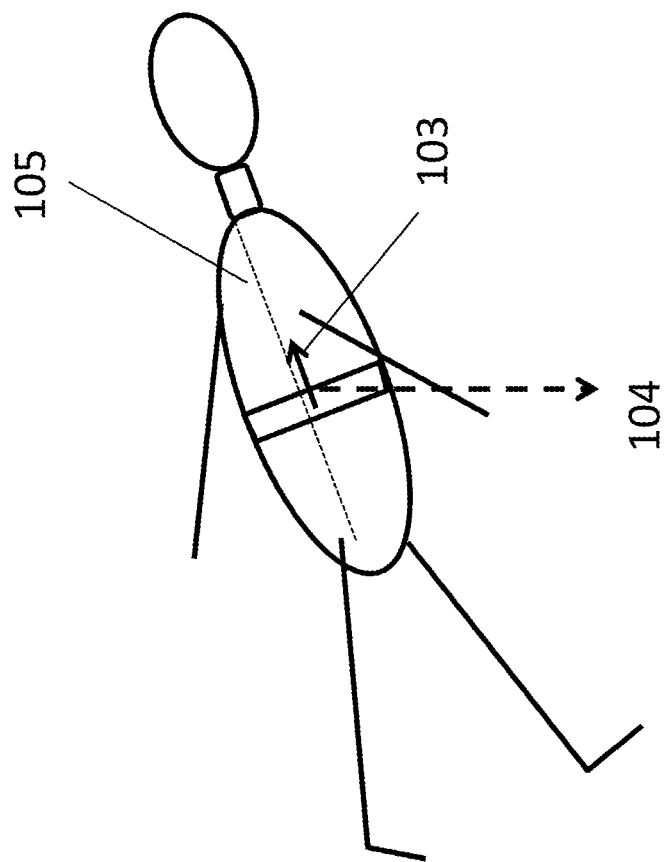
FIG. 1B illustrates the relative orientation of host body at fall down position with respect to local gravity direction, which can be detected by special designed sensor.
Figure 1A:
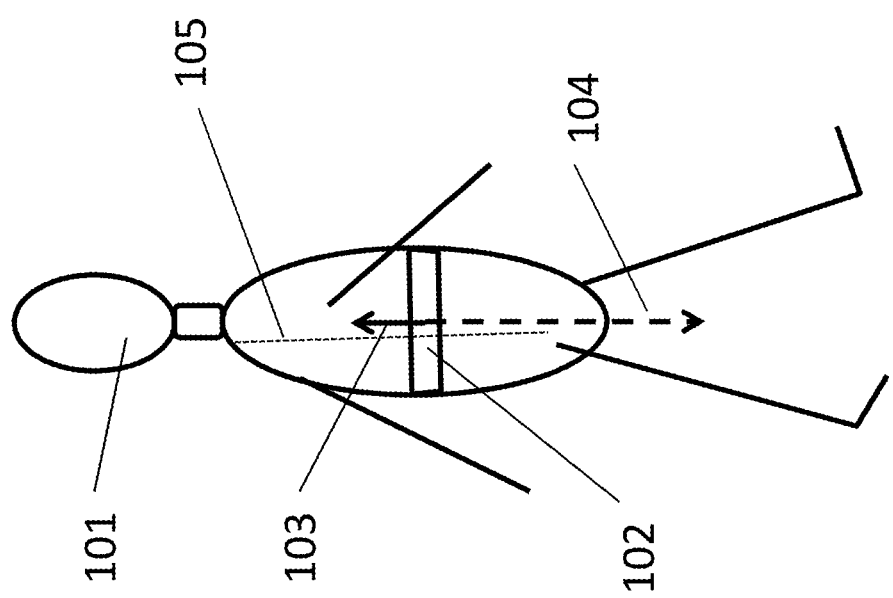
FIG. 1A illustrates the relative orientation of host body at normal walking position with respect to local gravity direction, which can be detected by special designed sensor.

FIG. 1A and FIG. 1B illustrate a fall detection mechanism by sensing the relative position or orientation change of host body with the direction of local gravity at the event of fall. The host can be anything such as a human, a robot, a ladder or a vehicle, whose fall is our major concern. The orientation of the host's body center-line can be used as a general reference for the body orientation of the host. It would be extremely reliable for a fall detection system to sensor only the change of the host's body center-line respective to the direction of local gravity, and ignore the details happened during the fall event.

In the particular scenario described here, the host is a human 101, whose spine 105 is used as a reference for the orientation of the human body. FIGS. 1A and 1B describes the situations before and after fall happens, respectively. It is quite noticeable that, regardless of the details of how the fall happens and the details of the speed or the acceleration before and after fall, the direction of local gravity 104 is not changed. However, the relative orientation between the host body (105) and direction of gravity (104), shown here as the angle between 105 and 104, has changed after fall happens.

Shown in FIG. 1A and FIG. 1B, a proposed sensor 102 is fixed on the waist of human body, whose orientation 103 parallel to the human body 105 is kept without change before and after fall. The change of the proposed sensor's orientation 103 respective to the direction of local gravity 104 precisely represents the orientation change of the host body 105 respective to the direction of local gravity 104. Hence, it would be extremely reliable to detect a fall event by sensing the change of the proposed sensor's orientation 103 respective to the direction of local gravity 104 and ignoring the details happened during the fall event.

Figure 2A:
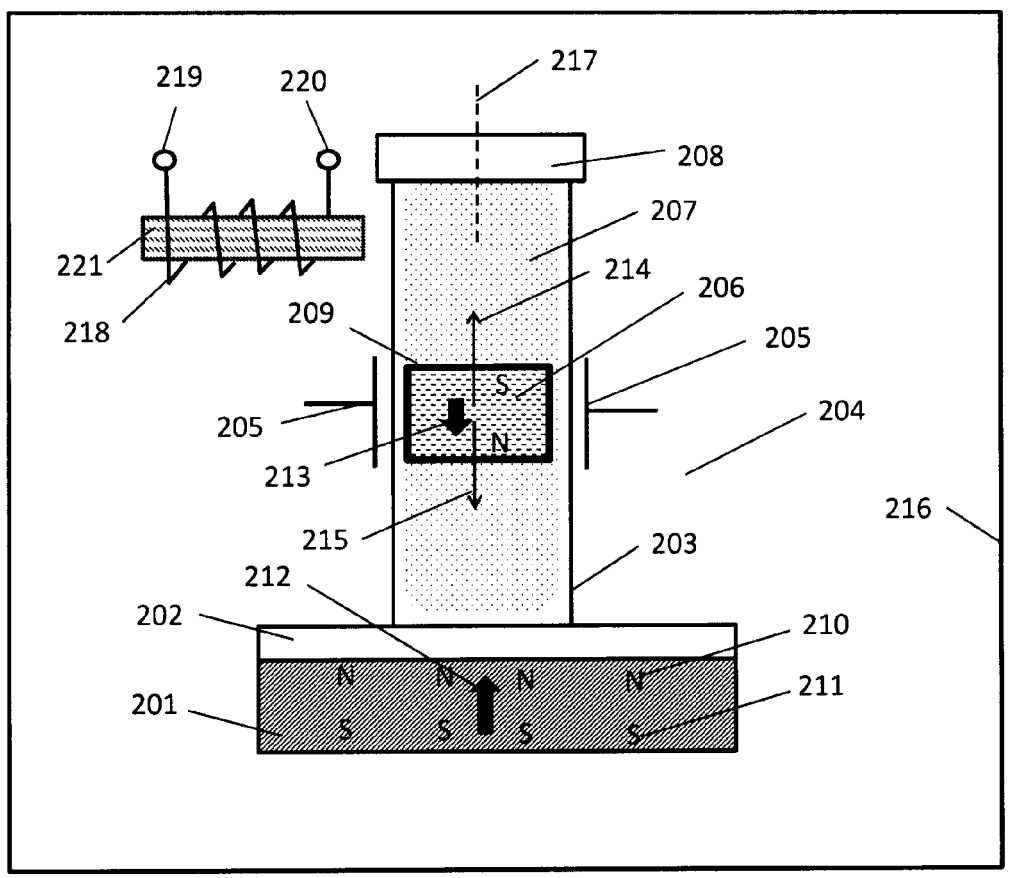
FIG. 2A illustrates one of the embodiments for the proposed sensor design.

FIG. 2A illustrates one of the embodiments for the proposed sensor design. The sensor comprises a bottom permanent magnet 201 (e.g. either a continue magnetic film or patterned magnet); an optional non-magnetic space layer 202; a hollow space in form of tube 203 formed within the dielectric matrix 204; a small permanent magnet 206, with coating layer 209 for reducing the friction between the magnet 206 and side wall of tube 203, floating inside tube 203; a lid 208 on top of the tube 203 to prevent the magnet 206 from moving out of the tube 203; and a pair of electrodes 205, which forms a capacitance sensor and locates in the vertical equilibrium position of magnet 206 when the center line 217 of tube 203 parallel to direction of local gravity 215. The magnetization 212 of the permanent magnet (or magnetic layer) 201 is aligned to be opposite to the magnetization 213 of the small magnet 206. The magnet 206 floats vertically inside tube 203 due to the magnetostatic repelling force 214 applied on magnet 206 from the permanent magnet 201 against the gravity 215 of the magnet 206 shown in FIG. 2A when the center line 217 of tube 203 parallel to direction of local gravity 215. Any interference or disturbing due to external magnetic field is shielded by the soft magnetic shield 216 around the sensor.

The capacitance between the pair of electrodes 205 is proportional to EA/d, while A is the facing area of the two electrodes 205, d is the distance of the two electrodes, and E is permittivity of material between the electrodes. The medium 207 filled inside the tube 203 can be air, a kind of gas, a kind of liquid, or even vacuum. The position of the magnet 206 in stable state inside the tube 203 varies with the orientation of the tube 203 respect to the gravity 215. Hence, the capacitance between the pair of electrodes 205 in stable state varies too with the orientation of the tube 203 respect to the gravity 215. The break of the force balance applied on the magnet 206, such as during falling, vibrating, or tilting, etc., will drive the magnet 206 away from its vertical equilibrium position inside the tube 203, resulting in the capacitance change between the pair of electrodes 205 due to the change of permittivity E. The dynamic response of the capacitance sensor can be used to detect a falling, tilting or vibrating event. Specially, the capacitance sensor can be used to sense a falling event by detecting the directional change of the center line 217 respect to the gravity 215. Multiple of capacitance sensor pairs can be arranged along the tube 203 to precisely detect the displacement of magnet 206 from its vertical equilibrium position inside tube 203 during the fall; and thus they can work together to define and characterize the fall event.

The coil 218 with optional soft magnetic core 221 is used to pick up the change of the magnetic flux within the coil 218 due to the move of the floating magnet 206. FIG. 2A shows one arrangement of the magnetic flux pickup coil 218. It locates on the top left side of the tube 203; and the axis of the coil 218 and its soft magnetic core 221 is perpendicular to the axis of the tube 217. The axis of the coil 218 and its soft magnetic core 221 can also be parallel to the axis of the tube 217. The magnetic flux pickup coil 218 can have different arrangements relative to the tube 203, such as on top of the tube 203, or on the right of the tube 203. The magnetic flux pickup coil 218 can also place at different latitude along the tube 203. The magnetic flux change within the magnetic pickup coil 218 is determined by the change of the floating magnet 206 position inside the tube 203; and the rate of the magnetic flux change is determined by the moving velocity of the floating magnet 206. According to Faraday's law, the output of the electromotive force (emf) voltage between the two leads 219 and 220 of the coil 218 is proportional to the rate of the magnetic flux change within the coil. Hence, any movement of the floating magnet 206 inside the tube 203 will trigger the dynamic output response of the coil's emf voltage.

Figure 2B:
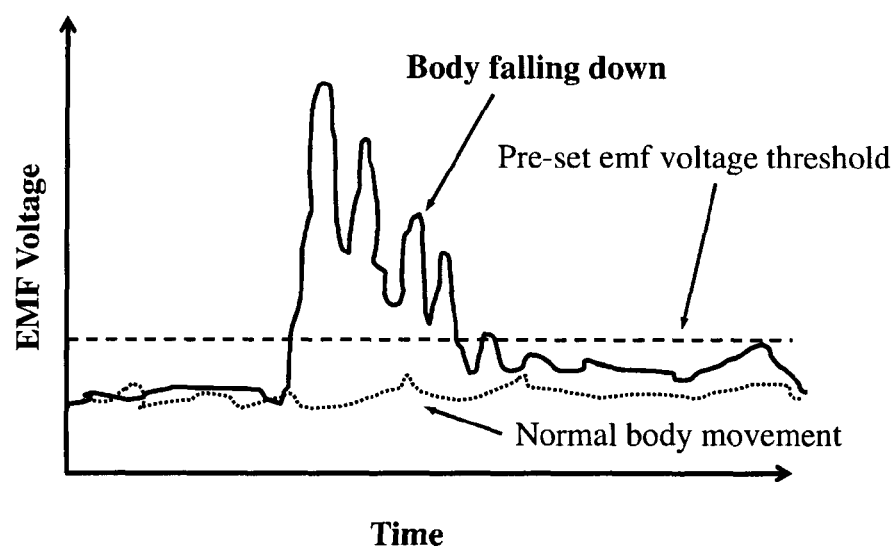
FIG. 2B illustrates the dynamic response of the output emf voltage of the magnetic flux pickup coil 218 shown in FIG. 2A to the host body's movement.
Figure 2C:
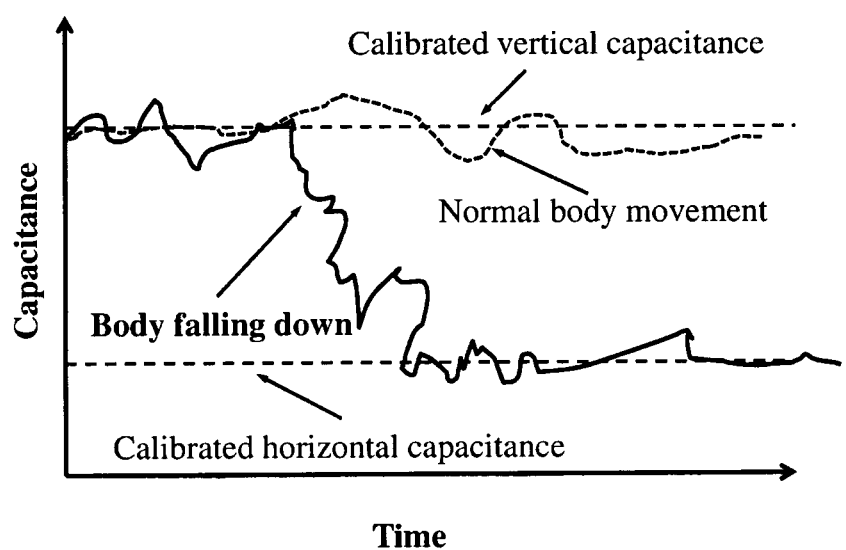
FIG. 2C illustrates the dynamic response of the capacitance of the capacitor 205 shown in FIG. 2A to the host body's movement.

For the application as a fall sensor, the device is tightly attached on the host body, and the centerline 217 of the sensor is always parallel to the centerline 105 of the host body shown in FIG. 1 before and after fall. Any host body's movement will cause the dynamic responses of the coil sensor 218 and capacitor sensor 205 shown in FIG. 2B and FIG. 2C, respectively. As shown in FIG. 2B, the output emf voltage of the coil sensor 218 breaks the pre-set threshold level (dash line), and dramatically increases at the beginning of the host body falling down due to large acceleration. It gradually drops down to below the pre-set threshold level at the end of the host body falling. For capacitor sensor 205, it has two distinct stable capacitance levels, i.e., calibrated vertical and horizontal capacitances respect to local gravity direction. The capacitance of the capacitor sensor 205 changes from its calibrated vertical level to its calibrated horizontal level when the host body falls down as shown in FIG. 2C. Continuously monitoring capacitor sensor 205 is not an economical operation mode due to its nature of energy consuming. Instead, as an economic operation mode, the fall sensor device continuously monitors the response of the coil sensor 218. The capacitor sensor 205 is used only at the end of a falling event detected by the coil sensor 218 to check whether the fall indeed happens or not. This approach is certainly the most reliable method to determine and sense the fall event.

All the structures and features shown here in FIG. 2A can be made by semiconductor process together with MEMS process, which is well known in the field. Therefore, volume manufacture as well as size reduction of the sensor become feasible with low cost.

Figure 3:
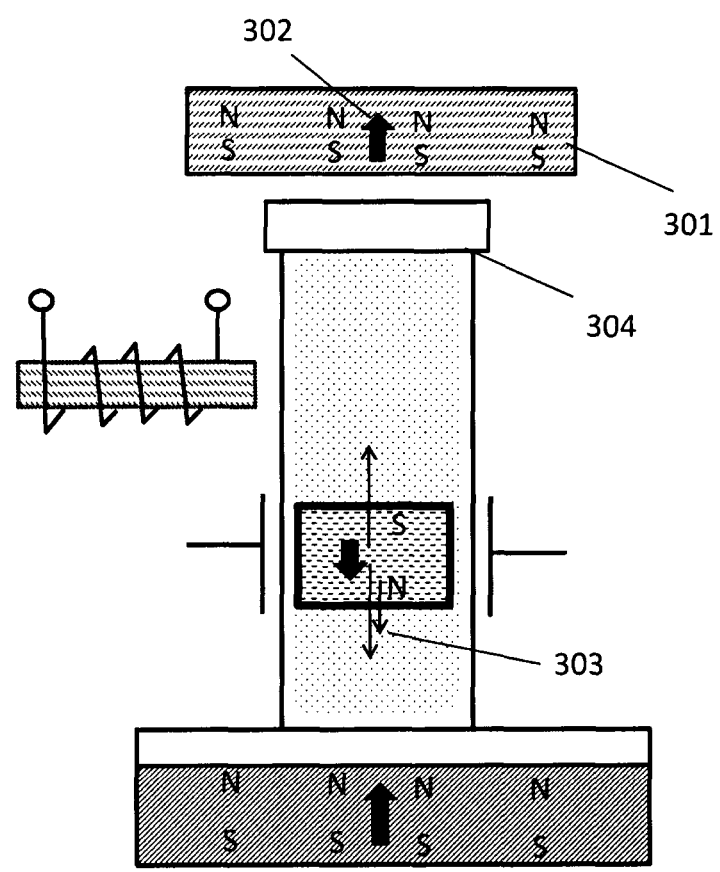
FIG. 3 illustrates one of the embodiments of sensor similar to that shown in FIG. 2 but with additional permanent magnet.

FIG. 3 illustrates one of the embodiments of sensor similar to that shown in FIG. 2A but with additional top permanent magnet 301. The magnetization 302 of the top permanent magnet 301 has the same direction as the magnetization 212 of the bottom permanent magnet 201, and is opposite to the magnetization 213 of the small magnet 206 inside the tube 203 shown in FIG. 2A. The magnetostatic force 303 pushing the small magnet inside the tube away from the top lid 304 prevents the small magnet inside the tube from touching (e.g. avoid noise generation) and sticking to the top lid 304. Moreover, this kind of design provides extra knobs to tune the sensitivity of the sensor by adjusting the position and/or strength of the magnet 301.

Figure 4A:
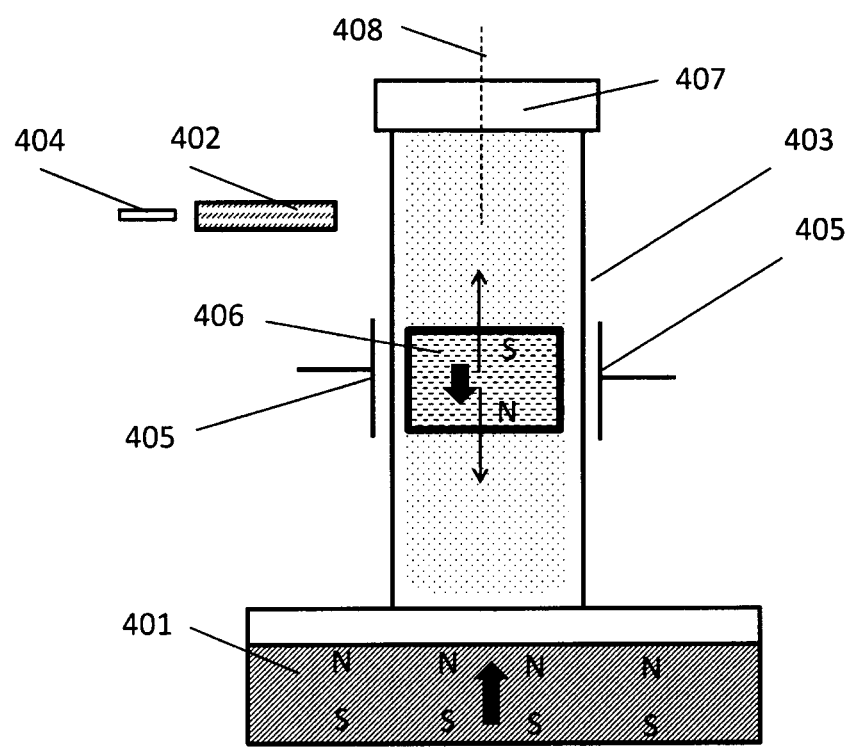
FIG. 4A illustrates one of the embodiments of the proposed sensor design.

FIG. 4A illustrates one of the embodiments of the proposed sensor design. The layout of the sensor shown in FIG. 4A is very much similar to what is shown in FIG. 2A. A bottom hard magnet 401 provides expelling magnetostatic force on the floating magnet 406 in the tube 403 to balance its gravity. The proposed sensor design shown in FIG. 2A detects the change rate of the magnetic flux within the magnetic flux pickup coil 218. The design shown in FIG. 4A is quite noticeably different from that shown in FIG. 2A. The solid magnetic field transducer 404 is used to detect the magnetic field strength regardless whether the magnetic field varies or not as long as the frequency of magnetic field variation is below a threshold value (e.g. GHz), which is well above the frequency we are interested in during fall event or the proposed applications. The magnetic field strength sensed by the solid magnetic field transducer 404 has a close correlation with the exact position of the floating magnet 406 in the tube 403 once the relative position of the transducer 404 to the tube 403 is fixed. Any movement of the floating magnet 406 inside the tube 403 will change the magnetic field strength that can be detected by the solid magnetic field transducer 404. The solid magnetic field transducer 404 can be a Hall sensor, a magneto-impedance (MI) sensor, an anisotropic magnetoresistive sensor (AMR), a giant magnetoresistive sensor (GMR), or a tunneling magnetoresistive sensor (TMR). The top of the tube 403 over the lid 407 is the best location for Hall Effect magnetic field transducer 404. For the proposed sensor design shown in FIG. 4A, the magnetic field strength sensed by the solid magnetic field transducer 404 can be enhanced by the optional structure of flux guide 402, which collects the magnetic flux from the floating magnet 406. Again, the electrodes 405 forms a capacitor sensor, which has the same function as that shown in FIG. 2A. The capacitor sensor 405 is an optional design feature since the field sensor alone is able to detect the all fall events.

For the application as a fall sensor, the device is tightly attached on the host body, and the centerline 408 of the sensor is always parallel to the centerline 105 of the host body shown in FIG. 1 before and after the fall. Any host body's movement, which could lead to potential fall event, will change the magnetic field strength. The change is detected by the transducer 404, and results in the oscillation output from the transducer 404. Depending on exact detecting algorithm, the frequency of the oscillation output, the amplitude variation (peak-to-peak value), or both together can be used to detect the fall event. The output changes of the transducer 404 from "above the pre-set threshold levels" to "below the pre-set threshold levels" indicate that either a real fall event or any possible event that could lead to possible falling has finished. The capacitor sensor 405 is used at the end of a falling event detected by the transducer 404 to check whether the fall indeed happens or not.

Actually, the field transducer 404 itself can be used alone to detect whether the fall indeed happens or not. As mentioned above, the field transducer 404 detects the magnetic field strength that is determined by the position of the floating magnet 406 inside the tube 403. Similar as the capacitor sensor 405, the field transducer 404 has two distinct stable outputs corresponding to the orientations of the tube 403 parallel or perpendicular to the gravity. At the end of any possible event, the field transducer 404 will have one stable output. By checking the final stable output of the field transducer 404, it can be relatively easy to deduce whether the fall indeed happens or not.

FIG. 4B to FIG. 4E describe three types of magnetoresistive sensors used as the transducer 404 in FIG. 4A.

Figure 4B:
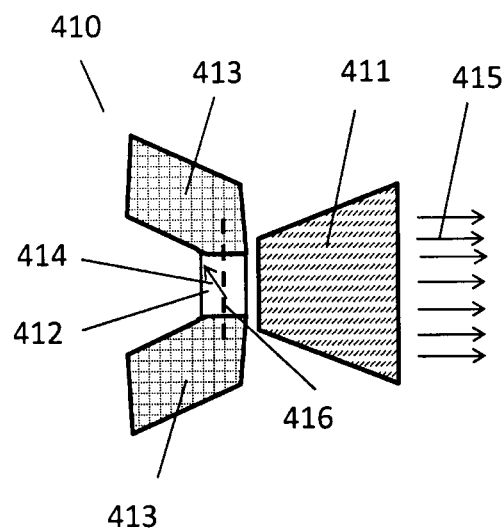
FIG. 4B illustrates the bird eye view of an AMR sensor used as the transducer 404 in FIG. 4A.

FIG. 4B illustrates the bird eye view of an AMR sensor used as the transducer 404 in FIG. 4A. The optional flux guide 411 concentrates incoming magnetic flux 415 towards AMR sensor 410 for improving its sensitivity. The AMR sensor 410 comprises two leads 413; AMR sensor stack 412, which has its sensing current 416 (indicated here by dash line) flowing between leads 413. The magnetization of the magnetic layer of AMR sensor stack 412, representing here by arrow 414, has a pre-fixed angle with the direction of the sensing current 416 in the absence of the external magnetic field. Any change of the magnetic field, due to the movement of the floating magnet 406 in FIG. 4A, leads to the change of the angle between the magnetization 414 and current 416 thus the output voltage of the AMR sensor 410 between leads 413. Therefore, the transducer based on AMR sensor described here is capable of detecting the movement as well as final location of the floating magnet 406 in FIG. 4A.

Figure 4C:
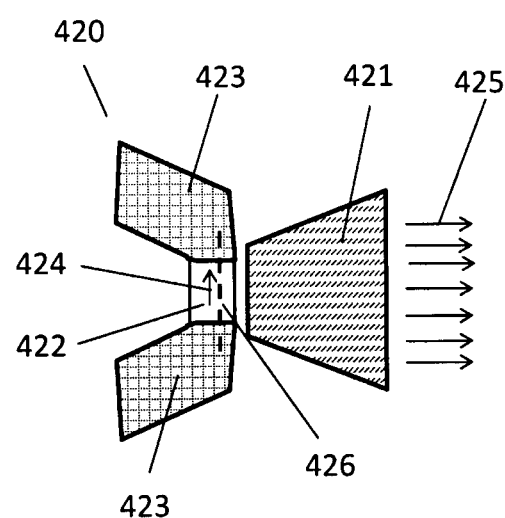
FIG. 4C illustrates the bird eye view of a GMR sensor used as the transducer 404 in FIG. 4A.

FIG. 4C illustrates the bird eye view of a GMR sensor used as the transducer 404 in FIG. 4A. The optional flux guide 421 concentrates incoming magnetic flux 425 towards GMR sensor 420 for improving its sensitivity. The GMR sensor 420 comprises two leads 423; GMR sensor stack 422, which has its sensing current 426 (indicated here by dash line) flowing between leads 423. The magnetization of the magnetic layer of GMR sensor stack 420, representing here by arrow 424, is aligned parallel with the sensing current 426 in the absence of the external magnetic field. Any change of the magnetic field, due to the movement of the floating magnet 406 in FIG. 4A, leads to the change of the angle between the magnetization 424 and current 426 thus the output voltage of the GMR sensor 420 between leads 423. Therefore, the transducer based on GMR sensor described here is capable of detecting the movement as well as final location of the floating magnet 406 in FIG. 4A.

Figure 4D:
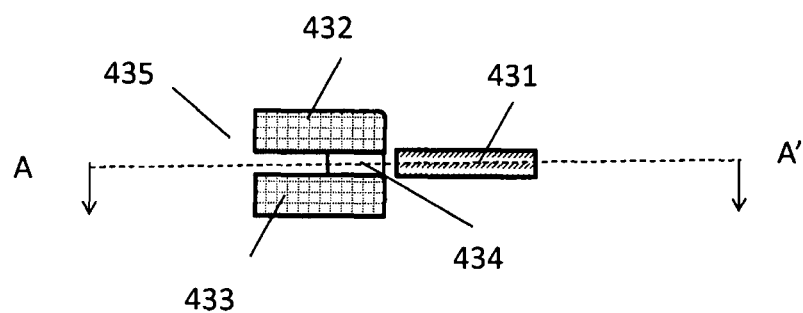
FIG. 4D illustrates the detailed zoom-in cross section view of a TMR sensor used as the transducer 404 in FIG. 4A.

FIG. 4D illustrates the detailed zoom-in cross section view of a TMR sensor used as the transducer 404 in FIG. 4A. The optional flux guide 431 is identical to the flux guide 402 shown in FIG. 4A. The TMR sensor 435 comprises bottom lead 433, TMR stack 434 and top lead 432.

Figure 4E:
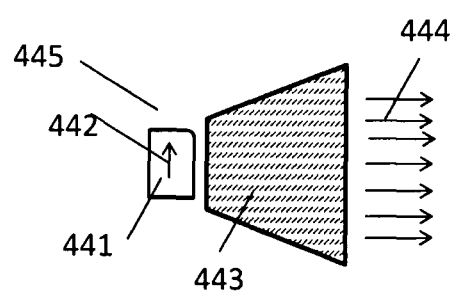
FIG. 4E illustrates the bird eye view of the TMR sensor cut along the line A-A' in FIG. 4D.

FIG. 4E illustrates the bird eye view of the TMR sensor cut along the line A-A' in FIG. 4D. The optional flux guide 443 concentrates incoming magnetic flux 444 towards TMR sensor 445 for improving its sensitivity. The TMR sensor 445 represents here by TMR free layer 441, which has its sensing current being perpendicular to the sensor free layer 441 flowing between lead 433 and 432 shown in FIG. 4D. The free layer 441 of TMR sensor 445 is aligned to the direction perpendicular to the potential incoming flux in the absence of the external field, and the alignment represents here by the arrow 442.

Any change of the magnetic field, due to the movement of the floating magnet 406 in FIG. 4A, leads to the change of the magnetization direction of the TMR free layer 441 resulting in the output voltage change between the electrodes 432 and 433 in FIG. 4D. Therefore, the transducer based on TMR sensor described here is capable of detecting the movement as well as final location of the floating magnet 406 in FIG. 4A.

Using TMR sensor as the transducer 404 in FIG. 4A can greatly increase the sensitivity of the proposed sensor. The TMR ratio can be as high as ~600%, which is similar to a big built-in hardware amplifier. The proposed ultra-high sensitivity TMR sensor illustrated here has significant advantages to detect very weak vibration of the surface, or very small angle titling such as building wall tilting. As a basic build sensing unit, it can construct a new type of sonar.

Figure 5:
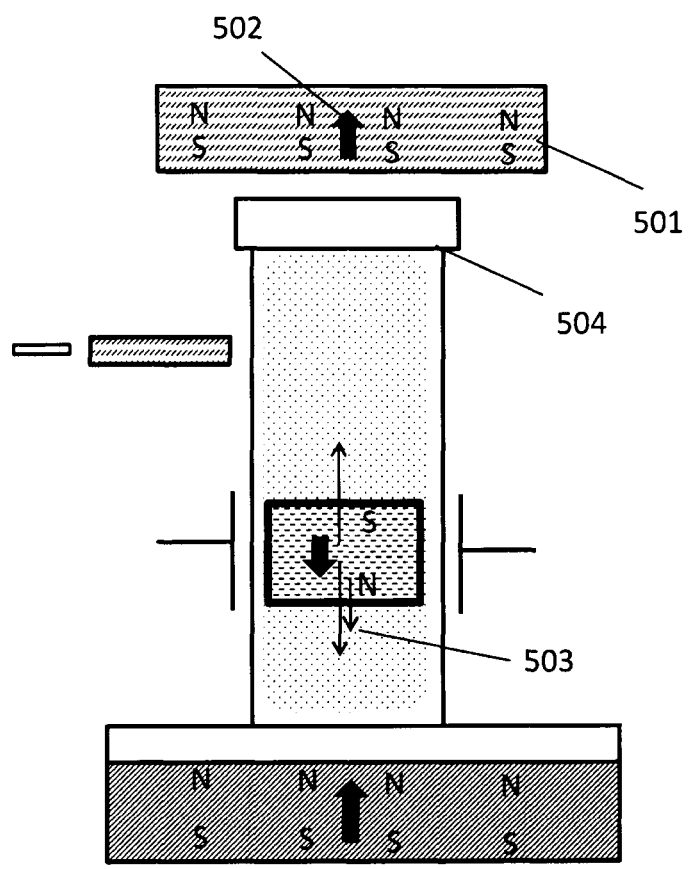
FIG. 5 illustrates one of the embodiments of sensor similar to that shown in FIG. 4A but with additional permanent magnet.

FIG. 5 to FIG. 4A is very much similar to the relationship between FIG. 3 to FIG. 2A. FIG. 5 illustrates one of the embodiments of sensor similar to that shown in FIG. 4A but with additional top permanent magnet 501. The magnetization 502 of the top permanent magnet 501 has the same direction as the magnetization of the bottom permanent magnet 401, and is opposite to the magnetization of the small magnet 406 inside the tube 403 shown in FIG. 4A. The magnetostatic force 503 as shown by the arrow pushing away the floating magnet 406 shown in FIG. 4A from the top lid 504 prevents the floating magnet from contacting and sticking to the top lid 504. Moreover, this kind of design provides extra knobs to tune the sensitivity of the sensor by adjusting the position and/or strength of the magnet 501.

Figure 6A:
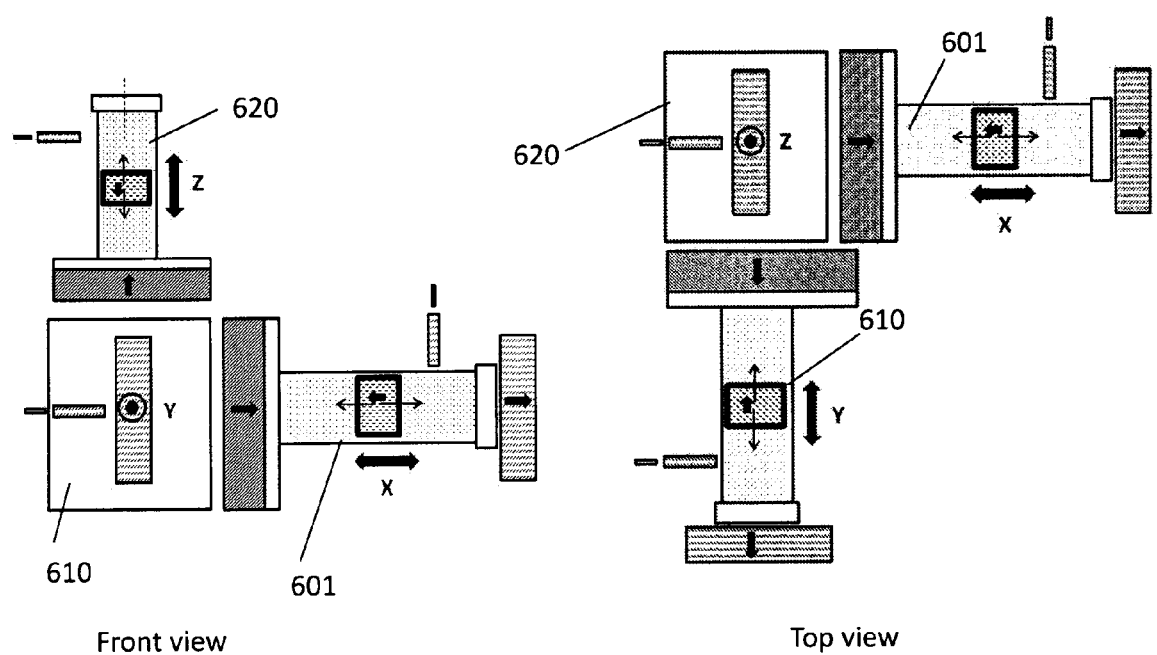
FIG. 6A shows a 3-sensor assembly that the sensors are assembled along 3 orthogonal X, Y and Z directions with front view on left and top view on right. All sensors come from design FIG. 2A, FIG. 3, FIG. 4A or FIG. 5.

FIG. 6A shows a 3-sensor assembly that the sensors are assembled along 3 orthogonal X, Y and Z directions with front view on left and top view on right. The sensors are chosen from above designs (FIG. 2A, FIG. 3, FIG. 4A or FIG. 5). Senor 601, 610 and 620 are assembled along 3-orthogonal X, Y and Z directions, respectively, which are magnetically isolated from each other to avoid their interferences. It is up to the assembly application on the choices of these 3 sensors designs.

Figure 6B:
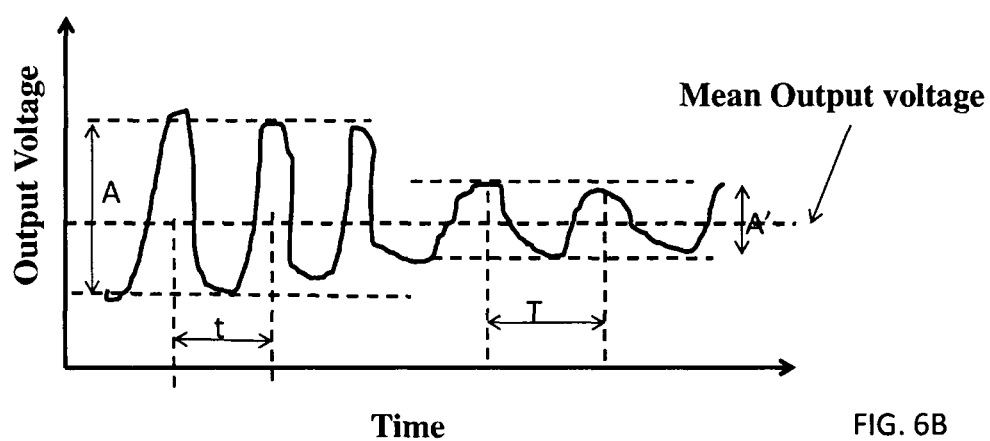
FIG. 6B illustrated a typical output from transducer of one sensor shown in FIG. 6A in time domain.
Figure 6C:
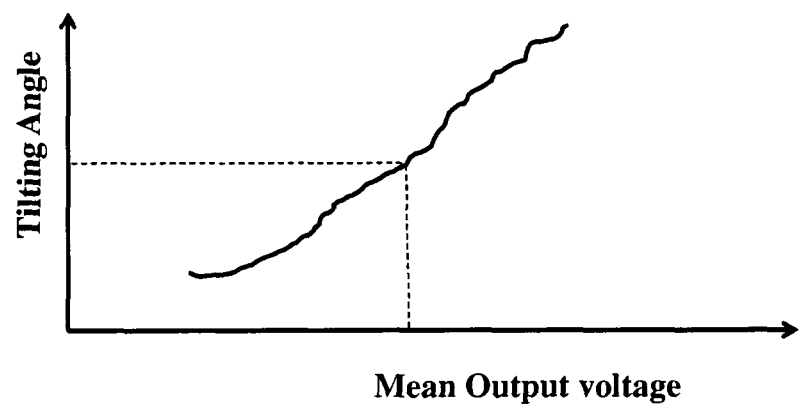
FIG. 6C illustrate the calibrated curve between the tilting angle of the sensor with respect to local gravity direction and the transducer mean output voltage from the sensor.

This kind of assembly configuration can be used for lots of applications. For example, the assembly can be used to monitor high building's tilting as well as the building's response to the local wind or earthquake in all directions. A typical output of one sensor is shown in FIG. 6B in time domain, and its corresponding tilting angle can be calibrated shown in FIG. 6C. All signals coming from 3 orthogonal directions can be used to monitor the high building's status, and detect its responses to the local wind or earthquake in all directions. Based on this technology, it is easy and economical to establish a sensor network inside the high building to monitor its safety, and set up its storm or earthquake emergency system.

This kind of sensor assembly can be used for athletic training too. Athlete's performance can be in-suit monitored and evaluated when lots of assemblies are attached on the athlete's body.

More sophistically, the dynamic information obtained by this kind of sensor assembly can be analyzed to detect all directions' vibrations. Hence, a new type of sonar can be constructed based on this technology to detect earthquake or tsunami.

Figure 7A:
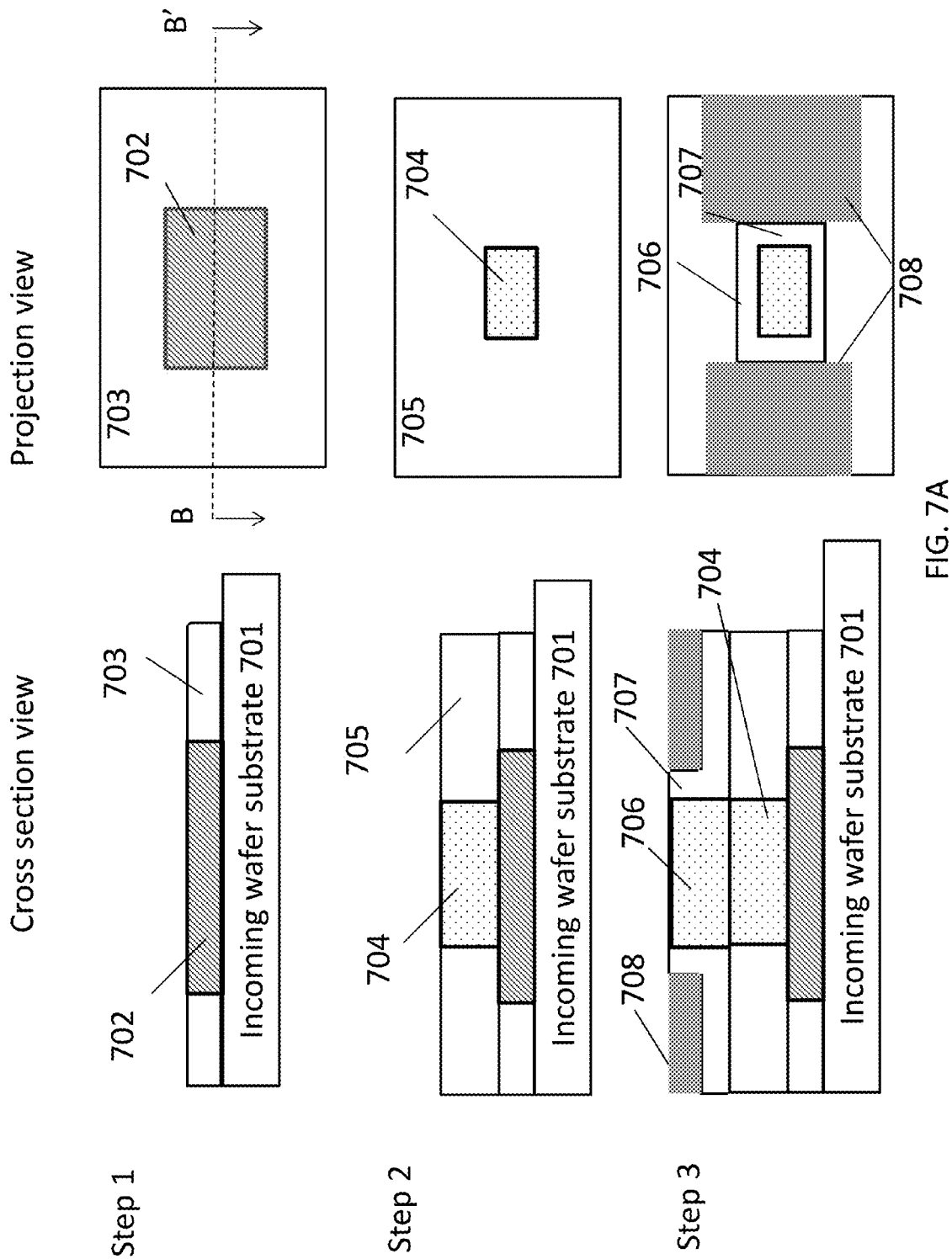
FIG. 7 illustrates wafer process to form the proposed sensor with the bottom magnet built on wafer.
Figure 7B:
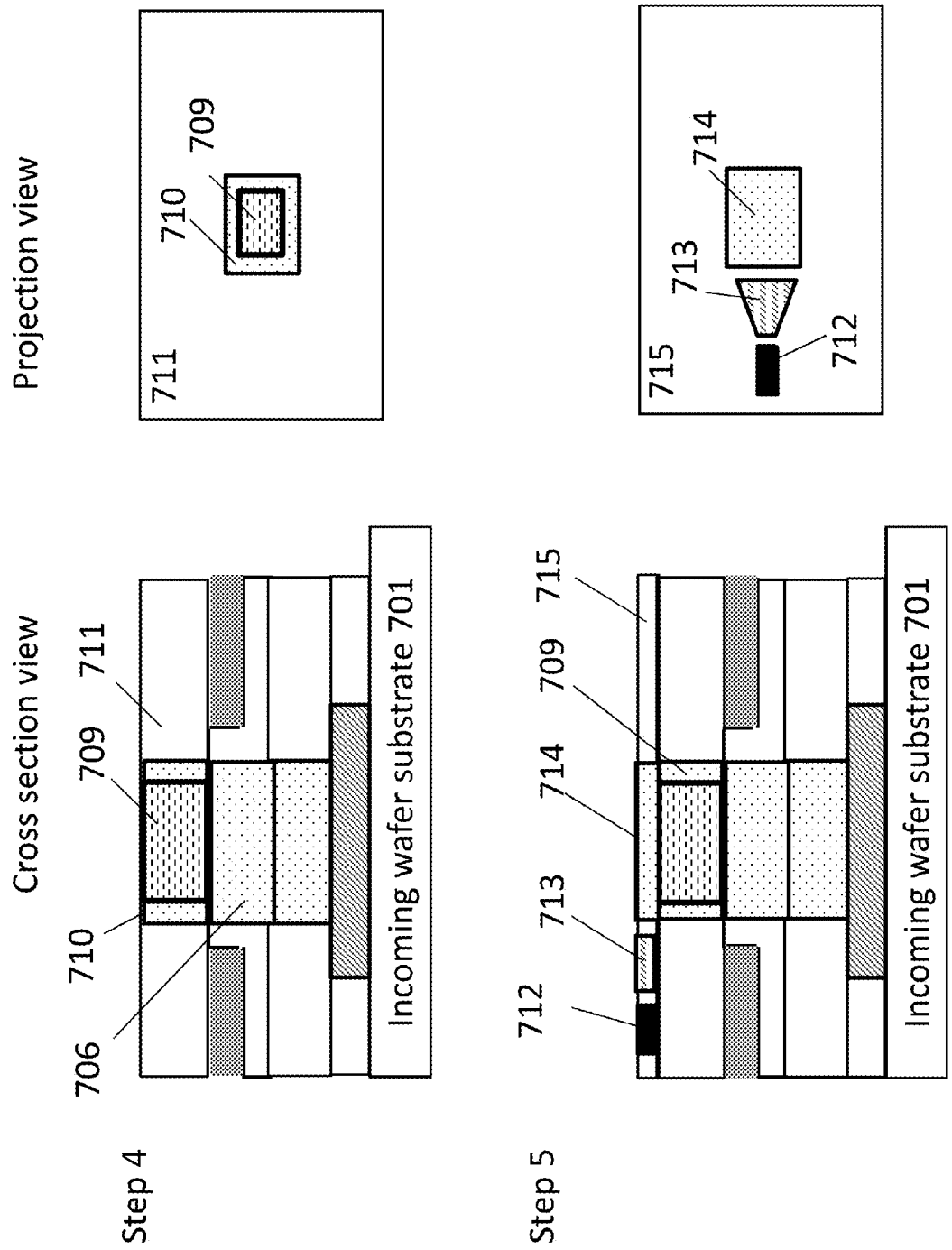

FIG. 7 is a schematic of the fabrication flow in wafer process to make one sensor proposed in FIG. 2A and FIG. 4A. It is easy to economically produce large volume of the devices in matured semiconductor/MEMS volume manufacture environment. Right side of drawings in FIG. 7 are the device project views at different key steps, and left side of drawings are the device cross section views along line B-B' in its project view drawings.

Firstly, the permanent magnet 702 with perpendicular magnetic anisotropy is built on the incoming wafer substrate 701. The material of the permanent magnet 702 can be sputtered alloy thin film, such as CoCrPt, CoPt, CoZrCrPt, etc., or sputtered multilayer film stack, such as Co/Cr, Co/Pt, Co/Pd, etc., or plated CoPt, CoNiMnP, CoNiReP, CoNiP film with proper seeding. The permanent magnet 702 can be a continue film or a patterned structure 702 shown in the Step 1 of FIG. 7. For the patterned permanent magnet 702, wafer surface has to be flatted for subsequent structure fabrications after the pattern formation. It can be carried out by a chemical mechanical planarization (CMP) process. Usually, SiO2 is chosen as the backfilled dielectric material 703 for wafer planarization.

The incoming substrate 701 can be ceramic wafer, glass wafer, plastic wafer, or normal semiconductor wafer such as normal Si wafer. Usually, normal semiconductor wafer is used as the material of the substrate 701. The Application-Specific Integrated Circuit (ASIC) for the sensor will be built-in first with proper electrical connections on the substrate 601. A special diffusion prohibited layer (diffusion barrier layer, such as Ni, W, $Ta_2O_5$.) will be deposited on top of the ASIC layer before the sensor fabrication to avoid any metallic contamination on the ASIC. For simplicity the electrical connections of the top sensor with the bottom ASIC are not included here. For other people familiar with semiconductor and MEMS wafer process, this can be done fairly easy.

Upon the formation of the permanent magnet 702 and surface planarization, a patterned sacrificial structure 704 shown in the Step 2 of FIG. 7 is built on the top surface of the permanent magnet 702 by semiconductor/MEMS microfabrication process, i.e., thin film deposition, photolithography pattern definition, and final pattern transfer by reactive ion etching (RIE), or photolithography pattern definition, thin film deposition, and final pattern formation by left-off process. The sacrificial structure 704 is enclosed by the backfill dielectric material 705, and planarized by CMP. The sacrificial structure 704 will be etched away later by a solution, leaving the backfill dielectric material 705 to form the 1st section (bottom) of the sensor's tube. The etching solution should not attack both the backfill dielectric material 705 and the bottom permanent magnet 702. In this disclosure, $Al_2O_3$ and $SiO_2$ are used for sacrificial and backfill dielectric materials, respectively, unless stated otherwise.

Next shown in Step 3 of FIG. 7, the $Al_2O_3$ sacrificial structure 706 surrounded by few hundred nanometers to a few or tens micrometers thick SiO2 material 707 is made first to form the 2nd section of the sensor's tube geometry, which is aligned with the 1st section (bottom) 704. And then, a pair of electrodes 708 is patterned and plated to form the capacitor sensor. The capacitor sensor is protected by the backfilled SiO2 material, and planarized by CMP.

Following the formation of the capacitor sensor, the small structure with hard magnet 709 is patterned and plated on the top of the sacrificial structure 706 shown in Step 4 of FIG. 7. Their centerlines are aligned together. The small hard magnet 709 is enclosed by $Al_2O_3$ sacrificial material 710; and the 3rd section of the sensor's tube is formed by backfilling $SiO_2$ material and CMP. PVD deposited Co alloy or plated CoPt can be used to make the small hard magnet 709 to ensure their coercivity Hare significantly different from that of the permanent magnet 702 from magnetics point of view.

The transducer 712, the optional magnetic flux guide 713, and the 4th sacrificial feature 714 are built by semiconductor/MEMS microfabrication process in Step 5 of FIG. 7. The sacrificial feature 714 is aligned with its bottom feature 709. They are protected by backfilled $SiO_2$ material 715. The surface is flatted by CMP for subsequent layer fabrication.

The sacrificial feature 716 built on the top of the 4th sacrificial feature 714 enclosed by backfilled $SiO_2$ material 719 will form the top section of the sensor's tube shown in Step 6 of FIG. 7. Both sacrificial features 716 and 714 are aligned together. After surface planarization, an addition sacrificial feature 717 and a sacrificial ring pattern 718 are built on the top of the feature 716. The sacrificial features 717 and 718 will be used to release the small hard magnet 709 after subsequently backfilled SiO2 material 720 and CMP. Finally, the sensor is sealed by depositing top layer SiO₂ material 621 after the release of the small hard magnet 709 by etching away all sacrificial materials in NaOH or KOH solution shown in Step 7 of FIG. 7.

For sensors proposed in FIG. 3 and FIG. 5, one more process step is needed to make a permanent magnet (301 in FIGS. 3 and 500 in FIG. 5) on top of the sensor.

Once the completion of the sensor fabrication magnetization alignments have to be performed in order to reach desirable magnetization directions. All 3 magnets (top and bottom permanent magnets and small floating hard magnet) will be aligned magnetically first in the same direction by applying a large magnetic field to along the long axle of the sensor tube. Then a smaller reversed magnetic field is applied to flip the magnetic orientation of the magnet(s) with lower coercivity ($H_c$) without disturbing the magnetic orientation of the magnet(s) with much higher coercivity so that the floating hard magnet and bottom or/and top magnet have opposite magnetization orientations.

Figure 8:
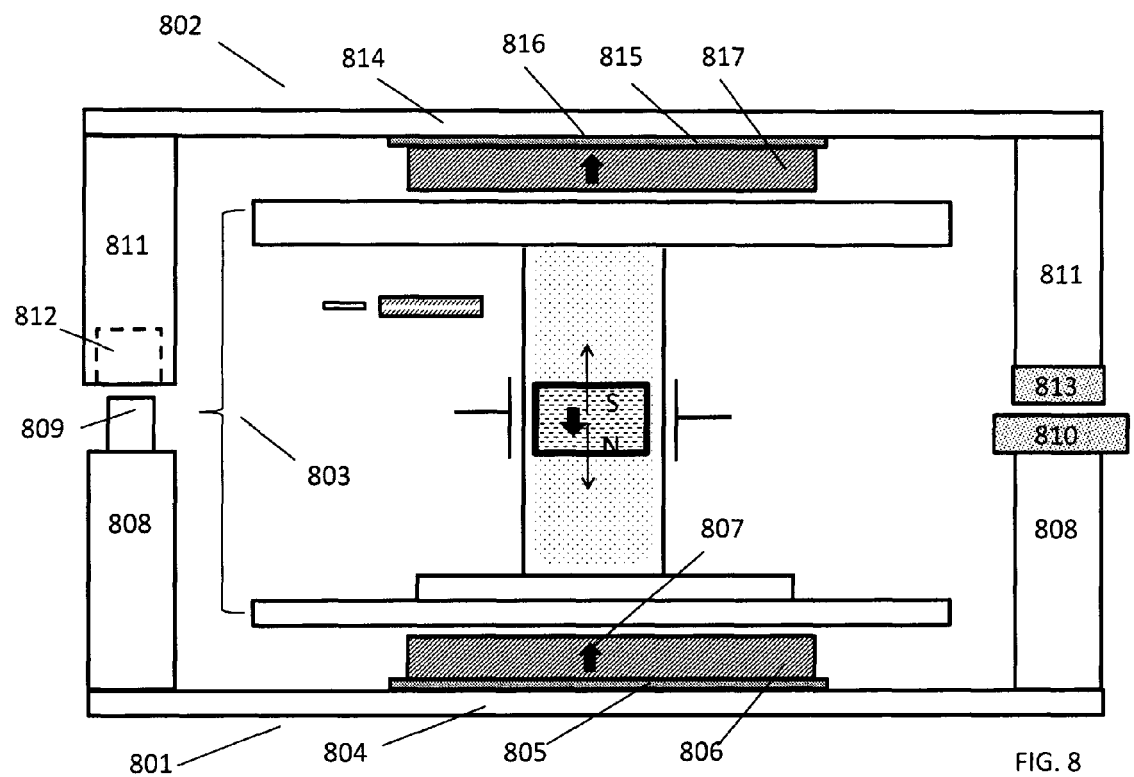
FIG. 8 illustrates a more cost friendly approach with the bottom magnet built in packaging component using conventional mechanical machining.

Alternatively, the manufactures of bottom permanent magnet (201 in FIG. 2A and 401 in FIG. 4A) and the top permanent magnet (301 in FIGS. 3 and 501 in FIG. 5) can be separated from the wafer process described above. As shown in FIG. 8, they can be made economically by classical massive mechanical machining alone, and packaged together with the sensor's key components fabricated by volume wafer processes described above.

FIG. 8 shows the whole package of the multi-purpose sensor including the bottom packaging frame 801, top packaging frame 802 and sensor body 803. The bottom packaging frame 801 comprises main body 804, non-magnetic bottom separation layer 805, bottom permanent magnet 806, bottom enclosing structure 808, bottom male mating connector 809, and solder pad 810. The top packaging frame 802 comprises main body 814, non-magnetic top separation layer 815, optional top permanent magnet 817, top enclosing structure 811, top female mating connector 812, and solder pad 813. From system reliability and stability points of view, soft magnetic material is preferred for the frame components of 804, 808, 809, 811, and 814 to shield the external magnetic field away from the sensor as well as to form a closed magnetic loop to further stabilize the internal magnetic configuration. The bottom and top magnetizations 807 and 816 are set in the same direction, which is opposite to that of the small floating hard magnet in the tube before the completion of the sensor packaging assembly. There are only one pair of mating connectors and one pair of solder pads shown in FIG. 8. On the really system, there are multiple pairs of mating connectors as well as solder pads to ensure solid packaging and closed magnetic loop formation.

What is claimed is:

1. A three-dimensional sensor system made from an assembly of three either semi- or fully independently oriented sensors, each of which is comprising:

An elongated hollow tube surrounded by dielectric material with a long axle;

A hard-magnet-containing floating structure, with a smaller cross section than that of the tube, whose magnetization points along said long axle of said elongated hollow tube;

At least a bottom hard magnet at one end of said elongated hollow tube, whose magnetization points oppositely to said hard-magnet-containing floating structure to provide a floating mechanism for said hard-magnet-containing floating structure;

A transducer sensing a magnetic field variation due to a movement of said hard-magnet-containing floating structure; and At least a pair of electrodes, built outside said elongated hollow tube, to detect a capacitance change due to the movement of said hard-magnet-containing floating structure.

2. The system of claim 1, wherein said transducer is a conductive coil with a soft magnetic core as a magnetic flux guide.

3. The system of claim 1, wherein said three-dimensional sensor system is enclosed within a soft magnetic shield to prevent the performance degradation due to the interference from an outside magnetic field disruption.

4. The system of claim 1, wherein said elongated hollow tube and said hard-magnet-containing floating structure have a different and yet asymmetric cross section design to reduce the friction force between them by minimizing their contact area.

5. The system of claim 4, wherein said asymmetric cross section design between said elongated hollow tube and said hard-magnet-containing floating structure prevents a flip of said hard-magnet-containing floating structure.

6. The system of claim 1, wherein said bottom hard magnet, is:

Either made monolithically using wafer fabrication processes;

Or manufactured by a classical mechanical machining then integrated on said three-dimensional sensor system.

7. The system of claim 1, wherein said three-dimensional sensor system is used as a sensor component for a digital lever.

8. The system of claim 1, wherein said three-dimensional sensor system is used to sense a vibration by attaching said assembly on three either semi- or fully independent surfaces.

9. The system of claim 8, wherein said vibration is caused by an earthquake or tsunami.

10. The system of claim 1, wherein said three-dimensional sensor system is used to measure a tilting angle from an original orientation, by attaching said assembly on three either semi- or fully independent surfaces and detecting a variation of a response from said assembly.

11. The system of claim 10, wherein said tilting angle is used to establish diagnostic sensing network system for a high building to monitor the building's safety and its dynamic responses in each direction to a local wind or an earthquake for a quick emergency response.

12. The system of claim 1 wherein said three-dimensional sensor system is used in an athletic training program to in-suit monitor and evaluate an athlete's performance by measuring said athlete's body movements.

13. The system of the claim 1, wherein each sensor of said assembly is fabricated in a volume manufacture monolithic wafer process environment comprising a sequence of key steps:

(a) Preparing a flat surface on a substrate, which has a built-in, pre-designed Application Specified Integrated Circuit for (ASIC) for the sensor, (b) Using either electroplating or physical vapor deposition to make said bottom magnet with a perpendicular magnetic anisotropy, (c) Etching temporary sacrificial material pattern to make said elongated hollow tube with few hundred nanometers to a few or tens micrometers thick wall to host said hard-magnet-containing floating structure, (d) Building said hard-magnet-containing floating structure, with perpendicular magnetic in a sacrificial pattern, whose coercivity is different from a coercivity of said bottom magnet which is later released from said sacrificial pattern by etching, (e) Building said transduce outside said elongated hollow tube, (f) Performing a magnetization alignment to establish a desired magnetic configuration for each key magnetic component, (g) Dicing said substrate and singularizing the die for said sensor.

14. The system of the claim 13, wherein said substrate is a semiconductor substrate.

* * * * *